United States Patent [19]

Wood et al.

[11] 4,042,589

[45] Aug. 16, 1977

[54] PTERIDINE COMPOUNDS

[75] Inventors: Hamish Christopher Swan Wood, Bearsden, Scotland; Kyuji Ohta, Tokyo, Japan

[73] Assignee: Burroughs Wellcome Co., Research Triangle Park, N.C.

[21] Appl. No.: 621,661

[22] Filed: Oct. 14, 1975

Related U.S. Application Data

[62] Division of Ser. No. 383,699, July 30, 1973, Pat. No. 3,933,820.

[30] Foreign Application Priority Data

Aug. 1, 1972 United Kingdom ............... 35816/72
Feb. 1, 1973 United Kingdom ................. 5190/73

[51] Int. Cl.$^2$ .......................................... C07D 475/04
[52] U.S. Cl. .................................................. 260/251.5
[58] Field of Search ...................................... 260/251.5

[56] References Cited

U.S. PATENT DOCUMENTS

| | | | |
|---|---|---|---|
| 2,656,356 | 10/1953 | Weisblat et al. ................... | 260/251.5 |
| 3,725,408 | 4/1973 | Wood et al. ....................... | 260/251.5 |
| 3,810,893 | 5/1974 | Wood et al. ....................... | 260/251.5 |
| 3,939,160 | 2/1976 | Stuart ................................ | 260/251.5 |

Primary Examiner—Paul M. Coughlan, Jr.
Attorney, Agent, or Firm—Donald Brown

[57] ABSTRACT

Novel pteridines of formula (I),

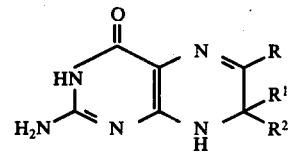

(I)

wherein R is an optionally substituted phenoxyalkyl group, and R$^1$ and R$^2$ are the same or different and each is a lower alkyl group or R$^1$ and R$^2$, together with the carbon atom, in the pteridine ring structure, form a spirocycloalkyl ring system having 4 to 6 carbon atoms outside the pteridine ring structure, and their method of preparation.

The above compounds have bacteriostatic activity.

16 Claims, No Drawings

PTERIDINE COMPOUNDS

This is a division of application Ser. No. 383,699, filed on July 30, 1973 now, U.S. Pat. No. 3,933,820.

The present invention relates to derivatives of pteridine, their chemical synthesis and pharmaceutical formulations containing them. The specification also describes compositions and pharmaceutical formulations comprising these pteridines in combinations which are useful in the treatment of microbial infections.

It is already established that the compounds 2-amino-4-hydroxy-6-hydroxymethyl-7,7-dimethyl-7,8-dihydropteridine and 2-amino-4-hydroxy-6-methyl-7,7-dimethyl-7,8-dihydropteridine or their tautomers or pharmaceutically acceptable salts thereof, have bacteriostatic activity, being particularly effective against *Cl. perfringens* and *Derm. dermatonomous,* as disclosed in the specifications of British Pat. No. 1303171 and Application No. 36289/70 (Belgian Pat. No. 770,577).

It has now been found that the novel pteridines represented by the following formula (I) or their tautomers or pharmaceutically acceptable salts thereof,

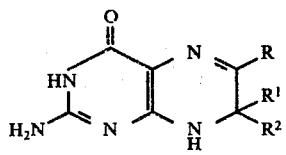

(I)

wherein R is an optionally substituted phenoxyalkyl group, and $R^1$ and $R^2$ are the same or different and each is a lower alkyl group or $R^1$ and $R^2$, together with the carbon atom in the pteridine ring structure, form a spirocycloalkyl ring system have 4 to 6 carbon atoms outside the pteridine ring structure, are also useful as antagonists of microbial metabolism. Furthermore these compounds may be useful as intermediates for the synthesis of the afore-mentioned 6-hydroxymethyl and 6-methyl substituted pteridines.

Although the phenoxyalkyl group is preferably unsubstituted and is most preferably a phenoxymethyl group, it may be substituted with one or more, advantageously one or two, alkoxy, amino, lower alkyl or hydroxyl groups or halogen atoms, in particular with a substitution in the para position. Compounds substituted with a methyl or methoxy group or a chlorine atom are of particular interest. Furthermore $R^1$ and $R^2$ are preferably lower alkyl groups and are most preferably the same and both methyl groups or ethyl groups. The compound 2-amino-4-hydroxy-6-phenoxymethyl-7,7-dimethyl-7,8-dihydropteridine is most preferred.

As used herein and throughout the specification, the terms lower alkyl group or alkoxy group refer to groups containing a straight or branched chain alkyl group having 1 to 4 carbon atoms.

According to the present invention, therefore, there are provided in one aspect the novel compounds of formula (I).

The above compounds and their salts inhibit one of the enzymes involved in the biosynthesis of dihydrofolic acid, namely hydroxymethyldihydropteridine pyrophophokinase, which is essential to the growth of microorganisms, for instance bacteria. They can thus be used in in vitro pharmacological investigations in clinical and diagnostic tests establishing, for instance, the properties of bacteria. When used as bacteriostats they may be present in a concentration of 50 to 500, in particular 110 to 180 mg of base/ml of the solution in which the organism grows in the absence of a compound. A further use of the compounds, when in solution, is in the treatment of wounds, for example after surgery, to prevent the growth of bacteria. Moreover the compounds of formula (I) and their salts manifest unexpectedly low toxicity in mammals or birds e.g. poultry, which makes them particularly suitable for application against microbial infections in such hosts under circumstances hereinbelow described.

Tetrahydrofolate co-factors are essential metabolites in all cells for the biosynthesis of purines, thymidylic acid, serine and several other biologically important compounds. Most of these co-factors are one-carbon adducts of tetrahydrofolic acid. The ultimate source of these for higher animals and man is food, containing preformed folates usually in the form of vitamins.

In microorganisms, the co-factors are synthesised from simpler chemicals. Generally the bio-synthetic process first provides dihydropteridine (Pt), i.e. 2-amino-4-hydroxy-6-hydroxymethyl-7,8-dihydropteridine (HMPt) pyrophosphate ester, from its immediate precursor HMPt in the presence of the enzyme hydroxymethyldihydropteridine pyrophosphokinase (HMPPS). Pt then condenses with p-aminobenzoic acid (pAB) in the presence of the enzyme dihydropteroate synthetase to form dihydropteroic acid (DPtA). This intermediate further condenses with a glutamate to form dihydrofolic acid (DFA or folate) which is then enzymatically reduced to provide the essential tetrahydrofolate in, for instance, bacteria and other microorganisms.

The provision of the folate from the basic building blocks, i.e. pteridine, pAB, and glutamate, and the further conversion of this into the tetrahydrofolate is known to be inhibited in two different ways. For instance sulphonamides displace pAB in the above reaction scheme. Because of their close structural resemblance to pAB, sulphonamides or similar other competitors enter the biosynthesis and prevent the formation of DPtA, and of DFA, and are therefore antimetabolites for the metabolite pAB. It is also known that compounds which are inhibitors of the enzyme dihydrofolic acid reductase block the synthetic step leading to tetrahydrofolate. A considerable number of pyrimidine derivatives show substantial anti-microbial properties on the basis of such blockage.

It was established later that such inhibitors may act synergistically with sulphonamides, i.e. there can be a sequential double blockade and a strong mutual potentiation of the anti-bacterial effects of the two materials. The range of anti-microbial action exerted by such combinations is considerably wider than that expected from the activity of either drug, and organisms which are only marginally sensitive to the individual agents become very sensitive to the combinations.

It was also suggested hypothetically that antimetabolites to Pt could inhibit the biosynthesis of DPtA (and DFA) (cf. Hitchings and Burchall *Advances in Enzymology,* 27, 417–468 (1965)) but compounds so far tested for the purpose have been disappointing, being either inactive or too toxic or sometimes both (cf. the compounds described in British Pat. Nos. 981,506 and 987,916).

It has been established that, for antimicrobial purposes, it is a prerequisite for the effective antagonism of Pt that the compound should be an inhibitor of HMPPS without also acting as an antimetabolite to the dihydropteridine that serves as a cofactor for the hydroxylation of phenylalanine and tyrosine, precursors of the catecholamines, such as norepinephrine, that have important actions as regulators of cardiovascular systems. Such an antimetabolic effect could lead to prohibitive toxicity to avian or mammalian species, which are normally the hosts infected with the microbes.

It has now been found that the compounds of formula (I) are their salts fulfil the above requirements i.e. inhibition of HMPPS combined with low toxicity to host species, as demonstrated for instance in chicks and rats. These compounds not only inhibit the growth of microorganisms on their own albeit to a limited extent with certain bacteria, such as *Staphylococcus aureus, Streptococcus pyogenes, Streptococcus faecalis, Escherichia coli, Salmonella typhi, Proteus vulgaris, Pseudomonas aerugenosa, Pasteurella multocida* among others, but have been found to act with a most remarkable synergistic effect when combined with a competitor of p-aminobenzoic acid, i.e. sulphonamides and similar compounds, or with selective inhibitors of dihydrofolic reductase, i.e. pyrimidines and related compounds, or with a combination of both of these types of antimicrobial agents. This potentiating effect of the compounds of formula (I) is the subject of co-pending cognate British Patent Application No. 36774/71 now, U.K. Pat. No. 1,405,246.

In that application there is described and claimed a composition for testing or treating microbial systems of infections, comprising an effective potentiating amount of a compound of formula (I) in combination with an effective amount of a competitor or inhibitor, or both, as herein defined.

The microbial infections against which these combinations are effective are protozoal or bacteria infections caused by those microorganisms which synthesise at least a substantial part of their tetrahydrofolate cofactor requirements. More specifically these infecting microorganisms are those which adequately absorb the pharmaceutical combinations disclosed herein and further are those in which these combinations have a synergistic effect in interfering with the de novo synthesis of the required tetrahydrofolate co-factors. For example, the compositions described have been found to be useful in the treatment of infections caused by *Staphylococcus aureus, Pseudomonas aerugenosa* and *Pasteurella multocida*.

It has been found specifically that, when compounds of formula (I) are combined with an amount of the competitor and/or the inhibitor which is not ordinarily sufficient to be effective as an antimicrobial agent in its own right, the combination of a compound of formula (I) with this normally ineffective amount of the competitor and/or the inhibitor provides a composition which in totality acts as an effective antimicrobial agent. This is especially notable when the amount of the compound of formula (I) is so low that it has substantially no microbial effect at the particular level, yet in the combination the potentiation is marked, in some instances very marked. Thus by using an effective potentiating amount of a compound of formula (I) together with the competitor and/or the inhibitor, it is now possible to reduce significantly the amount of the competitor and/or the inhibitor required to inhibit the growth of these bacteria.

In accordance with the above therefore, the term an effective amount used in conjuction with the terms a dihydrofolic reductase inhibitor and a para-aminobenzoic acid competitor means either (a) an amount of the inhibitor or competitor which is effective to a degree as an antimicrobial agent in its own right but which is potentiated by the use of a compound of formula (I) or (b) an amount of the inhibitor or competitor which is ineffective as an anitmicrobial agent but which when combined with a compound of formula (I) provides a composition which is an effective anti-microbial agent. An effective potentiating amount means an amount of the compound of formula (I) which increases the activity of an inhibitor and/or a competitor so as to provide an improved or adequate effectiveness for the whole combination.

It should be emphasised that the inhibition of the biosynthetic processes by such means could be termed as competitive antagonism in all three intances, and there might be potentiation between all three types of agents. The terms inhibitor, competitor, and potentiation by a compound of formula (I) are arbitrary and should only serve as convenient names for the appropriate type of components in combination products described and claimed in the specification of the aforementioned cognate application.

The inhibiting activity against HMPPS of a selected compound of formula (I) can, for instance, be tested by monitoring the transfer of the terminal phosphate of adenosine triphosphate ATP-$\gamma$-P$^{32}$ to dihydropteridine. It was found that the concentrations required for 50% inhibition of the formation of Pt (IC$_{50}$) in such tests are well correlated and within the margin of error obtained by other relevant tests in this respect, which measure the inhibition of either of the two enzymes involved in the formation of HMPt and DPtA. Such inhibition may, for instance, be easily and simply carried out by incubating an extract of *E. coli* with pAB-7-C$^{14}$, ATP, Mg and dihydropteridine. The formation of the dihydropteroate-C$^{14}$ can be quantitatively assayed after separating the unreacted pAB substrate, for instance by chromatography. It has been found that compounds possessing in such tests an IC$_{50}$ value of about 100$\mu$M, or less, usually below 50$\mu$M represent compounds exerting a useful potentiating effect, provided their toxicity in the appropriate vertebrates is acceptable. Preferably the value is 25$\mu$M or less, such as in the range between 2 to 12$\mu$M. Generally a value below 7$\mu$M is desirable.

As explained above, for the purpose disclosed it is essential that the compound of formula (I) should not have a prohibitive toxicity to the mammalian or avian hosts' cardiovascular systems. While low toxicity is therefore an essential requirement, a therapeutic index incorporates both the activity and toxicity values pertinent to the present disclosure and could be used with advantage for the selection of potentiating compounds of formula (I).

The therapeutic index is defined as the ratio of the maximum tolerated dose to the minimum effective dose and in most cases is preferably greater than 10, suitably at least 5 and in exceptional circumstances at least about 3 for humans, but possibly as low as 2 for animals.

Although the art is aware of many compounds which are known competitors of para-aminobenzoic acid and are antimicrobials, the sulphur compounds which are disclosed as antimicrobial agents from the top of page 994 to page 1007 of the Merck Index, 8th Edition, 1968 are presented by way of example only.

Of the known compounds which are competitors, the following sulphonamide compounds (or pharmaceutically acceptable salts thereof) are preferred for the purpose described.

Sulphanilamide, sulphadiazine, sulphamethisazole, sulphamethizole, sulphapyridine, sulphathiazole, sulphamerazine, sulphamethazine, sulphisoxazole, sulphadoxine, sulphasomidine, sulphachlorpyridazine, 2-(p-aminobenzene)sulphonamido-3-methoxypyrazine(-Kelfizina), a-amino-p-toluenesulphonamide, 5-sulphanilamido-2,4-dimethyl pyrimidine, 4-(N'-acetyl sulphanilamido)-5,6-dimethoxy pyrimidine, 3-sulphanilamido-4,5-dimethyl isoxazole, 4-sulphanilamido-5-methoxy-6-decyloxy pyrimidine, sulphamonomethoxine, 4-p-(8-hydroxy-quinilinyl-4-azo)-phenyl sulphanilamido-5, 6-dimethoxy pyrimidine, sulphadimethoxine, sulphamethoxazole, sulphaquinoxaline, and p-(2 methyl-8-hydroxy-quinolinyl-(5)-azo)phenyl sulphanilamido-5,6-dimethoxy pyrimidine. Examples of a non-sulphonamide type of competitor are p-amino salicylic acid (PAS) and p,p'-diaminodiphenylsulphone.

Similarly, although many compounds are known which inhibit dihydrofolic reductase and act as antimicrobial agents, the compounds disclosed in the following patents are presented by way of example of compounds suitable for use for the purpose disclosed.

U.S. Pat. Nos. 2,658,897; 2,767,183; 3,021,332; 2,937,284; 3,322,765; 2,909,522; 2,624,732; 2,579,259; 2,945,859; 2,576,939; 2,926,166; 2,697,710; 2,747,345; and 2,749,344.

The following inhibitors (or pharmaceutically acceptable salts thereof) are preferred for the combinations described, however:

2,4-diamino-6-ethyl-5-p-chlorophenylpyrimidine (pyrimethamine), 2,4-diamino-5-(3'4',5'-trimethoxybenzyl)-pyrimidine (trimethoprim), 2,4-diamino-5-(3'4'-dimethoxybenzyl) pyrimidine (diaveridine), 2,4-diamino-5-(2'-isopropyl-4'-chlorophenoxy) pyrimidine, 2,4-diamino-5-methyl-6-sec-butylpyrido (2,3-d) pyrimidine, 2,4-diamino-5-methyl-6-benzylpyrido(2,3-d) pyrimidine, 2,4-diamino-6-benzylpyrido(2,3-d) pyrimidine, 2,4-diamino-5,6-trimethylenequinazoline, 2,4-diamino-5,6-tetramethylenequinazoline, 2,4-diamino-5-(2',4'5=trimethoxybenzyl) pyrimidine, 2,4-diamino-5(2'-ethyl-4',5-dimethoxybenzyl) pyrimidine, 2,4-diamino-5-(2'-methyl-4',5'-dimethoxybenzyl) pyrimidine.

However, the most preferred combinations include those combining a compound of formula (I), especially that wherein R is a phenoxymethyl group and $R^1$ and $R^2$ are both methyl groups, with sulphadiazine, sulphamethoxazole, sulphadoxine or sulphaquinoxaline as competitors, or with trimethoprim, diaveridine or pyrimethamine as inhibitors. In view of possible synergistic advantages of using certain competitors and inhibitors in combination against particular diseases, and the potentiating effect of compounds of formula (I) on both of these types of antibacterial compounds, it has been preferred to formulate triple combinations, comprising a compound of formula (I) with one of the above-mentioned preferred competitors, and one of such inhibitors. For example, combinations of sulphadiazine/trimethoprim, sulphamethoxazole/trimethoprim, sulphadoxine/ trimethoprim or sulphaquinoxaline/diaveridine, each together with a compound of formula (I), give improved effectiveness when compared with the components alone or with pairs of them.

The compounds of formula (I) either alone or together with the competitor and/or the inhibitor, may be presented in association with a carrier in pharmaceutical formulations suitable for parenteral, topical, rectal or oral administration. The formulations for oral or rectal administration are advantageously presented in discrete units, such as tablets, capsules, cachets, ampoules or suppositories, each containing a predetermined amount of each compound, but may also be presented as a powder, as granules, as a solution of suspension in an aqueous or non-aqueous liquid, or as an ointment or paste for topical administration. For parenteral use, the formulations incorporating an aqueous or non-aqueous liquid carrier must be sterile and be presented in sealed containers. The formulations may be made by any of the known methods and may include one or more of the following accessory ingredients:

diluents, solutes to render the solution isotonic with the blood, buffers, flavouring, binding, dispersing, surface-active, thickening, lubricating and coating materials, preservativees, bacteriostats, antioxidants, suppository and ointment bases, and any other acceptable excipients.

In another aspect of the present invention, therefore, there is provided a pharmaceutical formulation comprising a compound of formula (I) in combination with a pharmaceutically acceptable carrier. In yet another aspect the present invention provides a method of making a pharmaceutical formulation by admixing the compound of formula (I) with a carrier by known techniques. The specification of the afore-mentioned cognate application further discloses and claims a pharmaceutical formulation comprising a composition, as hereinbefore defined, together with a carrier, and its method of preparation, by admixing the composition with the carrier by known, techniques.

Formulations containing the compound of formula (I) in association with a competitor or an inhibitor may also be presented in the form of a kit, which comprises separately packaged units or dosages of these components with instructions for use in a combined form. The instructions may also specify the manner of administration and indications for which the formula is suitable.

The compounds of formula (I), either for use alone or in association with a competitor and/or inhibitor, and also the competitors and inhibitors, may be presented in the form of their pharmaceutically acceptable salts of a mineral or organic acid, for example hydrochloric acid, hydrobromic acid, sulphuric acid, acetic acid, citric acid, tartaric acid, lactic acid, maleic acid or salicylic acid, or, especially for the sulphonamide competitor, of a base, such as sodium hydroxide, potassium hydroxide, tetramethyl ammonium hydroxide or ammonia.

The ratios in which the therapeutically active compounds of formula (I) are utilized in the compositions described in this specification can be varied between wide limits. Depending on the nature and circumstance of use, the compositions may contain the compound of formula (I) with the competitor and/or the inhibitor in appropriate proportions and dosages. For instance, in cases of uses in vivo it is often desirable to maintain a certain proportion of components in the blood serum or tissue fluids, preferably for a prolonged period. Depending on the various absorption, discharge or decomposition rates of the components, the initial quantities and proportions of the ingredients of the formulation can be different from that aimed at in the tissues in vivo. The formulations and dosages recommended for the general treatment of a particular human or animal disease must be adjusted according to the particular requirements of the recipients of the disease, the known activities of the competitor or inhibitor component against the causative organism, the half life and the toxicity of the components in vivo, and other practical requirements.

For example the composition or pharmaceutical formulation may contain from about 1 to 30 parts by weight, preferably 5 to 15 parts, of the compound of formula (I), or an equivalent amount of a salt thereof, and 1 to 30 parts, preferably 5 to 15 parts, of a competitor, or an equivalent amount of a salt thereof, and/or one part of an inhibitor, or an equivalent amount of a salt thereof.

Dosage will vary depending upon the infecting organism but under ordinary circumstances up to about 60 mg/kg each of a compound of formula (I) and competitor, and up to about 7.5 mg/kg of inhibitor, in combination, can be administered daily in several doses. The composition or pharmaceutical formulations can be administered to human potentials in unit dosage forms which contain up to 750 mg of the compound of formula (I), and up to 750 mg of the competitor and/or up to 25 mg of the inhibitor. Preferably for adult dosages the amount of the compound of formula (I) would be about 200 mg, that of the competitor about 200 mg and/or that of the inhibitor about 25 mg.

The pharmaceutical formulation comprising the compound of formula (I) in combination with the competitor and/ or the inhibitor is also usable in solution for irrigating wounds, for example after surgery, so as to prevent the growth of bacteria. For example, an antibacterial solution having the following preferred concentration of components may be used:

1–30 mg/ml of the compound of formula (I), 1–30 mg/ml of the competitor and/or 0.03–1 mg/ml of the inhibitor, in a pharmaceutically acceptable solvent, suitable for external use.

The potentiating effect of compounds of formula (I) can be demonstrated and utilized in vitro relatively easily for research and practical purposes. Such possibilities include diagnosis and the identification of the bacterial flora of individuals and the consequential selection of clinical treatment schedules.

The various combinations can be incorporated in porous discs (such as filter paper discs) or in Agar Nutrient or other media for bacterial growth for determining susceptibility. Those articles incorporating the compound of formula (I) with a competitor and/or an inhibitor compound may be distributed or sold to doctors, hospitals and clinics for the above purposes. A typical testing disc may be impregnated with a solution containing 5 to 50 μg/ml of a para-aminobenzoic acid competitor, 0.5 to 5 μg/ml of a dihydrofolic reductase inhibitor, and about 10 to 100 μg/ml of a compound of formula (I) in a medium comprising a mixture of an aqueous infusion and papain digest or horse muscle.

Furthermore, such pharmacological tests involving potentiated competitors or inhibitors may also be useful for the characterisation of bacteria according to their sensitivity and to their particular resistance for instance to a competitor when used alone, and such investigations involving a variety of formulations as described herein also form the basis of determining the compositions of selected formulations for general treatment purposes. The toxicity of compounds of formula (I) is generally considerably lower than that of the competitors or inhibitors commonly used, which may enable the clinician to maintain or increase the effectiveness of the antibacterial activity of the formulation with a concurrent increase of the therapeutic ratio or decrease in the toxic or side-effects of the medicament.

In addition to the above, compounds of formula (I) have been found to potentiate the activity of the aforementioned competitors and/or inhibitors against infections with microorganisms in domestic animals, including poultry, for example against *Pasteruella multocida* but especially against the protozoal disease coccidiosis. Such triple formulations comprising a compound of formula (I) together with a compound such as sulphaquinoxaline and an inhibitor such as diaveridine are effective in lower concentrations than the competitor or inhibitor components alone and possess an enhanced activity, being effective against all relevant Eimeria species causing this disease in poultry.

The compounds of formula (I) may be prepared by the reductive cyclisation of a compound of formula (II),

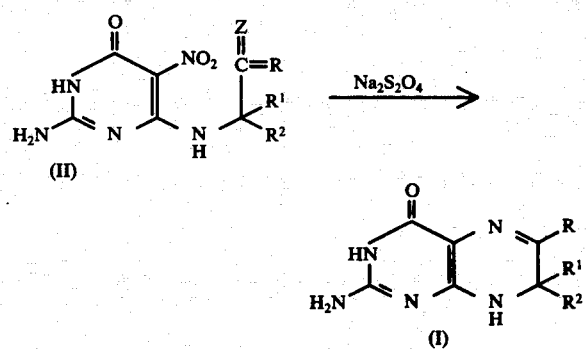

wherein R, $R^1$ and $R^2$ are as defined above and Z is a ketonic oxygen atom or a protecting group therefor, such as a semicarbazone group or an oxime group, prepared according to the procedures disclosed by Pfleiderer and Zondler (Chem. Ber. 99, 3008 (1966) and the specifications of British Pat. No. 1,303,171 and of copending British Pat. Application No. 36289/70 (Belgian Pat. No. 770,577) respectively.

The method described in British Pat. Application No. 36289/70, however, is particularly preferred.

In this method, a compound $R^1R^2C = CHR$ (VI), wherein R, $R^1$ and $R^2$ are as defined above, undergoes an addition reaction with a nitrosyl halide, prepared in situ, and the resulting nitrosohalide (V) is converted to the oxime (IV) by reaction with ammonia solution. Reacting the oxime (IV) with a 2-amino-4-halogeno-6-hydroxy-5-nitropyrimidine (III) provides the pyrimidine ketoxime (II) which is then reductively cyclised to give then pteridine (x), as shown in the following sequence.

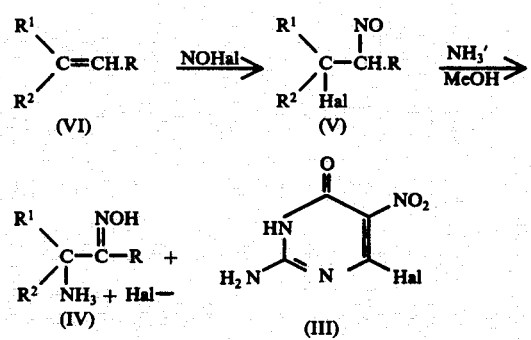

-continued

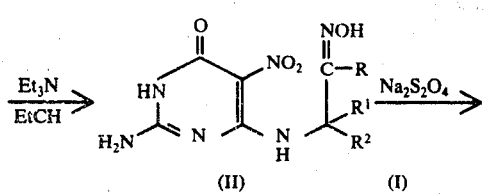

The compound (VI) may in turn be prepared by reaction of the corresponding halide of formula (VII), wherein n is an integer from 1 to 4, with an alkali metal phenoxide, optionally substituted in the phenyl ring, in the presence of a polar solvent. The halide (VII) may be prepared from the halogenation corresponding primary alcohol (VIII) by with an appropriate agent, such as a phosphorus trichloride or thionyl chloride. The alcohol (VIII) may itself be obtained by reduction of a carboxylic acid or ester derivative, e.g. (IX), with a powerful reducing agent, such as lithium aluminium hydride or sodium dihydrobisethoxymethoxy aluminate. Alternatively the tertiary alcohol, e.g. (X), resulting from the reaction of a ketone, e.g. (XI), with an allylic Grignard reagent, may be halogenated to produce the halide (VII). The above sequence is illustrated below for the preparation of an optionally substituted phenoxymethyl derivative, but the higher homologues may be prepared analogously.

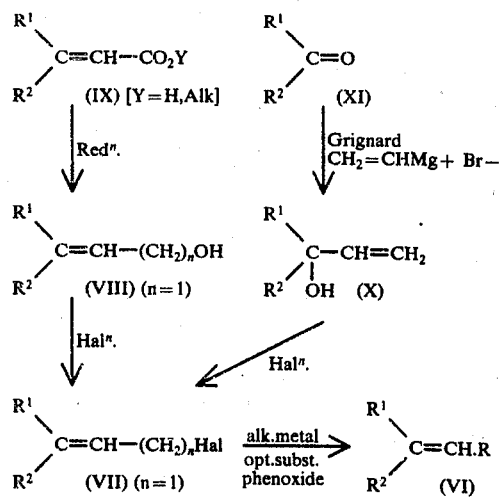

It will be seen from the above that in the preparation of compounds of formula (I) wherein the phenoxyalkyl group is substituted as hereinbefore defined, the phenyl ring in the alkali metal phenoxide should already contain these substituents in the desired position. If a compound having $R^1$ and $R^2$ as different substituents is required, the nitrosohalide (V) will contain a racemic mixture of two stereoisomers, in view of the asymmetric carbon atom present. Separation of these isomers by conventional techniques well known in the art may advantageously be effected at this stage prior to reaction with the ammonia solution.

According to the present invention in further aspects there are also provided:

1. The methods described herein for preparing any of the compounds of formula (I), comprising effecting reductive cyclisation of the compounds of formula (II).

2. The methods described herein for preparing any of the compounds (II), wherein Z is an oxime group, from (IV), (IV) from (V) or (VI) and (VI) from (VII).

3. Compounds of formula (I), (II), wherein Z is an oxime group, (IV) and (VI), whenever prepared by a method as defined under (1) or (2).

4. As novel compounds of value as chemical intermediates; compounds of formula (II), (IV) and (V).

5. A pharmaceutical formulation comprising a compound of formula (I) or a salt thereof in combination with a pharmaceutically acceptable carrier, whenever prepared by the method herein described.

The following examples illustrate the invention but are in no way intended to limit the scope of the invention. Temperatures are in degrees Celsius.

EXAMPLE A.

2-Amino-4-hydroxy-6-phenoxymethyl-7,7-dimethyl-7,8-dihydropteridine (I; R = $CH_2OC_6H_5$, $R^1 = R^2 = CH_3$)

i. 1-phenoxy-3-methylbut-2-ene (VI; R = $CH_2OC_6H_5$, $R^1 = R^2 = CH_3$)

A mixture of phenol (18.8 g) and sodium hydroxide (8 g) was stirred at 60°–70° in dimethylformamide (162 ml) and water (18 ml) while 1-bromo-3-methylbut-2-ene (VII, $R^1 = R^2 = CH_3$, HAL = BR) (29.8 g) was added dropwise over 1½ h. The mixture was stirred at 60° for 4 h after the addition was complete. It was then poured into water (800 ml) and extracted with ether (3 × 300 ml). The ether extract was washed with 10% sodium hydroxide (200 ml) and then with water (3 × 200 ml) before drying over anhydrous sodium sulphate. The solvent was removed in vacuo, and the residue distilled to give 1-phenoxy-3-methylbut-2-ene (2.4 g, yield 75%) as clear liquid b.p. 116°–118°/18 mm. Hg.

ii. 2-Chloro-4-phenoxy-2-methyl-3-nitrosobutane (V; R = $CH_2OC_6H_5$, $R^1 = R^2 = CH_3$)

Concentrated hydrochloric acid (7.8 ml) was added dropwise over 1 h to a mixture of 1-phenoxy-3-methylbut-2-ene (VI) (12.6 g) and amyl nitrite (11.7 ml) in glacial acetic acid (15.6 ml) at 0° (ice-salt bath). A white precipitate separated and this was filtered off and dried to give the nitrosochloride (V) (12.8 g, yield 73%) as colourless crystals, m.p. 134°. The nitrosochloride can be recrystallised from acetone but this is not necessary.

iii. 3-Amino-1-phenoxy-3-methylbutan-2-one oxime hydrochloride (IV; R = $CH_2OC_6H_5$, $R^1 = R^2 = CH_3$)

A suspension of 2-chloro-4-phenoxy-2-methyl-3-nitrosobutane (V) (17.2 g) in methanol (approx. 300 ml) was refluxed while ammonia gas was bubbled through the suspension. Methanol was added from time to time to keep the volume of the solution approximately constant. After 6 h the solution was evaporated, and the residue after washing with acetone gave the ketoxime hydrochloride (IV) (12.1 g, yield 65%) as colourless crystals, m.p. 238°–240° (decomp.) iv. 2-Amino-4-hydroxy-6-[2-hydroxyimino-3-phenoxy-1,1-dimethylpropylamino]-5-nitropyrimidine (II; R = $CH_2OC_6H_5$, $R^1 = R^2 = CH_3$)

A mixture of 2-amino-4-chloro-6-hydroxy-5-nitropyrimidine (III) (Hal = C l) (4.8 g), 3-amino-1-phenoxy-3-methylbutan-2-one oxime hydrochloride (IV) (6.12 g) and dry triethylamine (5.45 g) in dry ethanol (50 ml) were refluxed for 2 h. The mixture was cooled, water (150 ml) was added, and the resulting precipitate was filtered off and dried. Recrystallisation from water gave the nitropyrimidine oxime (II) (5.45 g. yield 57%) as pale yellow plates, m.p 210° (decomp.).

v. 2-Amino-4-hydroxy-6-phenoxymethyl-7,7-dimethyl-7,8-dihydropteridine (I; R = CH₂OC₆R₅, R¹ = R² = CH₃)

A solution of 2-amino-4-hydroxy-6-(2-hydroxyimino-3-phenoxy-1,1-dimethylpropylamino)-5-nitropyrimidine (II) (3.6 g) in water (100 ml) and 2M sodium hydroxide (20 ml) was warmed on a steam bath. Sodium dithionite (6.3 g) was added portionwise until an almost colourless solution was obtained. Glacial acetic acid was added to the solution to adjust to pH 4, and the mixture was heated for 1 h. The solution was cooled and the dihydropteridine (I) (2.0 g. yield 67%) was collected by filtration, m.p. >260° (decomp.).

EXAMPLE B.

2-Amino-4-hydroxy-6-(p-methoxy)phenoxymethyl-7,7-dimethyl-7,8-dihydropteridine (I; R = CH₂OC₆H₄.OCH₃, R¹ = R² = CH₃)

i. 1-p-methoxy)phenoxy-3-methylbut-2-ene (VI; R = CH₂OC₆H₄.OCH₃, R¹ = R² = CH₃)

A mixture of p-methoxyphenol and sodium hydroxide was stirred with dimethylformamide and water while 1-bromo-3-methylbut-2-ene(VII; R¹ = R² = CH₃, Hal = Br) was added dropwise. The mixture was stirred, poured into water and extracted with ether. The ether extract was washed with 10% sodium hydroxide and then with water before drying over anhydrous sodium sulphate. The solvent was removed in vacuo, and the residue distilled to 1-(p-methoxy)phenoxy-3-methylbut-2-ene (VI).

ii. 2-Chloro-4-(p-methoxy)phenoxy-2-methyl-3-nitrosobutane (V; R = CH₂OC₆H₄.OCH₃, R¹ = R² = CH₃)

Concentrated hydrochloric acid (8.1 ml) was added dropwise over 10 minutes to a mixture of 1-(p-methoxy)phenoxy-3-methylbut-2-ene (VI; R = CH₂OC₆H₄.OCH₃, R¹ = R² = CH₃) (16.05 g) and amyl nitrite(12.1 ml) in glacial acetic acid (16.2 ml) at −5° to 0° (ice-salt bath). After a further 1 hour at −5° to 0°, the mixture was filtered. The solid so obtained was washed with acetone and recrystallised from acetone to give the nitrosochloride (V) (4.87 g, yield 22%) as pale yellow crystals, m.p. 123° (decomp.).

iii. 3-Amino-1-(p-methoxy)phenoxy-3-methylbutan-2-one oxime hydrochloride (IV, R = CH₂OC₆H₄.OCH₃, R¹ = R² = CH₃)

A suspension of 2-chloro-4-(p-methoxy)phenoxy -2-methyl-3-nitrosobutane (V) (4.803 g) in dry methanol (80 ml) was heated to reflux while ammonia gas was passed through until all the solid dissolved (3.5 h). Filtration and removal of solvents gave an off-white solid, which was largely freed of impurities by washing with benzene. Two recrystallisations from isopropanol (a small inorganic residue remained) gave the ketoxime hydrochloride (IV) (2.77 g, yield 53%) as colourless crystals, m.p. 219°-220° (decomp.).

iv. 2-Amino-4-hydroxy-6-[2-hydroxyimino-3-(p-methoxy)phenoxy-1,1-dimethylpropylamino]-5-nitropyrimidine (II; R = CH₂OC₆H₄.OCH₃, R¹ = R² = CH³)

A mixture of 3-amino-1-(p-methoxy)phenoxy-3-methylbutan-2-one oxime hydrochloride (IV) (2.748 g), 2-amino-4-chloro-6-hydroxy-5-nitropyrimidine (III) (Hal = Cl) (1.906 g) and dry triethylamine (4.1 g) was heated to reflux in dry ethanol (120 ml) for 17 hours. 120 ml water was added and the mixture was heated to effect solution, filtered and cooled. The filtrate on removal of some solvents under reduced pressure deposited the nitropyrimidine oxime (II) (1.77 g) as a tan solid m.p >250° (decomp.).

v. 2-Amino-4-hydroxy-6-(p-methoxy)phenoxymethyl-7,7-dimethyl-7,8-dihydropteridine (I; R = CH₂OC₆H₄.OCH₃, R¹ = R² = CH₃)

A solution of 2- amino-4-hydroxy-6-[2-hydroxyimino-3-(p-methoxy)phenoxy-1, 1-dimethylpropylamino]-5-nitropyrimidine (II) (1.60 g) in warm 1 M sodium hydroxide (80 ml) was treated during 25 minutes with sodium dithionite (8 g) in portions until no red colour remained. A pink solid was removed and the filtrate was acidified with glacial acetic acid. Most of the solvents were removed under reduced pressure. Treatment with methanol and filtration, concentration of the filtrate and repetition gave and alcoholic concentration from which the dihydropteridine (I) separated as pale needles.

EXAMPLE C.

2-Amino-4-hydroxy-6-(p-methoxy)phenoxymethyl-7,7-dimethyl-7,8-dihydropteridine (I; R = CH₂OC₆H₄.OCH₃, R¹ = R² = CH₃)

i. 1-(p-methoxy)phenoxy-3-methylbut-2-ene (VI; R = CH₂OC₆H₄OCH₃, R¹ = R² CH₃)

1-Bromo-3-methyl-but-2-ene (VII; R¹ = R² = CH₃) was added dropwise to a mixture of p-methoxyphenol and sodium hydroxide in dimethylformamide and water and the 1-(p-methoxy)phenoxy-3-methylbut-2ene (VI) extracted as described under Example B(i)

ii. 2-Chloro-4-(p-methoxy)phenoxy-2-methyl-3-nitrosobutane (V; R = CH₂OC₆H₄.OCH₃, R¹ = R² = CH₃)

Concentrated hydrochloric acid (7.8 ml) was added dropwise over 1 hour to a mixture of 1-(p-methoxy)-phenoxy-3-methylbut-2-ene (VI; R = CH₂OC₆H₄.OCH₃, R¹ = R² = CH₃) (12.0 g) and amyl nitrite (11.7 ml) in glacial acetic acid (15.6 ml) at 0° C (ice-salt bath). A white precipitate separated and this was filtered off and dried to give the nitrosochloride (V) (8.0 g, yield 50%) as colourless crystals, m.p. 137°.

iii. 3-Amino-1-(p-methoxy)phenoxy-3-methylbutan-2-one oxime hydrochloride (IV; R = CH₂OC₆H₄.OCH₃, R¹ = R² = CH₃)

A suspension of 2-chloro-4-(p-methoxy)phenoxy-2-methyl-3-nitrosobutane (V) (4.0 g) in methanol (approx. 80 ml) was refluxed while ammonia gas was bubbled through the suspension. Methanol was added occasionally to keep the volume of the solution approximately constant. After 6 hours the solution was evaporated and the residue, after washings and acetone, gave the ketoxime hydrochloride (IV) (3.2 g, yield 75%) as colourless crystals, m.p. 225° iv. 2-Amino-4-hydroxy-6-[2-hydroxyimino-3-(p-methoxy)phenoxy-1,1-dimethyl-propylamino]-5-nitropyrimidine (II; R = CH₂OC₆H₄.OCH₃, R¹ = R² = CH₃)

A mixture of 2-amino-4-chloro-6-hydroxy-5-nitropyrimidine (III) (Hal =C l) (1.53 g), 3-amino-1-(p-methoxy)phenoxy-3-methylbutan-2-one oxime hydrochloride (IV) (2.29 g) and dry triethylamine (1.70 g) in dry ehtanol (20 ml) was refluxed for 2 hours. The mixture was cooled, water (50 ml) was added, and the resulting precipitate was filtered off and dried. Recrytallisation from a mixture of water and ethanol gave the nitropyrimidine oxime (II) 4.9 g. yield 48%) as pale yellow crystals, m.p. 242° (decomp.).

v. 2-Amino-4-hydroxy-6-(p-methoxy)phenoxymethyl-7,7-dimethyl-7,8-dihydropteridine (I; R = CH$_2$OC$_6$H$_4$.OCH$_3$, R$^1$ = R$_2$ = CH$_3$)

A solution of 2-amino-4-hydroxy-6[2-hydroxyimino-3-(p-methoxyphenoxy-1,1-dimethyl-propylamino]-5-nitropyrimidine (II) (0.5g) in water (15 ml) and 2 M sodium hydroxide (3) was warmed on a steam-bath. Sodium dithionete (1.0 g) was added portionwise until an alomost colourless solution was obtained. Glacial acetic acid was added to the solution to adjust to pH4, and the mixture was heated for 1 hour. The solution was cooled and the solid (0.250 g) was filtered off. The solid was heated in dimethylformamide (40 ml) for 2 hours on the steam bath. Filtration of the cooled reaction mixture gave the dihydropteridine (I) (0.18 g. yield 40%) m.p. 274°–276° (decomp.)

EXAMPLE D

2-Amino-4-hydroxy-6-(p-chloro)phenoxymethyl-7,7-dimethyl-7,8-dihydropteridine (I; R = H$_2$OC$_6$H$_4$. Cl, R$^1$ = R$^2$ = CH$_3$)

i. 1-(p-chloro)phenoxy-3-methylbut-2-ene (VI; R = CH$_2$OC$_6$H$_4$.Cl, R$^1$ = R$^2$ = CH$_3$)

This compound was prepared following the general procedures described under Example B(i), using p-chlorophenol as starting material instead of p-methoxyphenol.

ii. 2-Chloro-4-(p-chloro)phenoxy-2-methyl-3-nitrosobutane (V; R = CH$_2$OC$_6$H$_4$.Cl, R$^1$ = R$^2$ = CH$_3$)

Concentrated hydrochloric acid (28.4 ml) was added dropwise over 1 hour to a mixture of 1-(p-chloro)phenoxy-3-methylbut-2-ene (VI; R=CH$_2$OC$_6$H$_4$.Cl, R$^1$ = R$^2$ =CH$_3$) (56.1 g) and amyl nitrite (42.6 ml) in glacial acetic acid (56.7 ml) at −5° to 0° (ice-salt bath). After a further 1 hour at −5° to 0°, the mixture was filtered. The solid so obtained was washed with benzene and recrystallised from benzene after drying to give the nitrosochloride (V) (35.31 g, yield 47%) as pale yellow crystals, m.p. 124°–5° (decomp.).

iii. 3-Amino-1-(p-chloro) phenoxy-3-methylbutan-2-one oxime hydrochloride (IV; R = CH$_2$OC$_6$H$_4$.Cl, R$^1$ = R$^2$ = CH$_3$)

A suspension of 2-chloro-4-(p-chloro)phenoxy-2-methyl-3-nitrosobutane (V) (34.20 g) in dry methanol (375 ml) was heated to reflux while ammonia gas was passed through until all the solid dissolved (9.5 hours). Filtration and removal of the solvents gave a brown solid, which was largely freed of impurities by washing with benzene. Recrystallisation from isopropanol (a small inorganic residue remained) gave the ketoxime hydrochloride (IV) (19.65 g, yield 54%) as colourless crystalls, m.p. 225°–227° (decomp.).

iv) 2-Amino-4-hydroxy-6-[2-hydroxyimino-3-(p-chloro)phenoxy-1,1-dimethylpropylamino]-5-mitropyrimidine (II; R = CH$_2$OC$_6$H$_4$.Cl, R$^1$ = R$^2$ = CH$_3$)

A mixture of 3-amino-1-(p-chloro)-phenoxy-3-methylbutan-2-one oxime hydrochloride (IV) (5.58 g), 2-amino-4-chloro-6-hydroxy-5-nitropyrimidine (III) (Hal = Cl) (3.81 g) and dry triethylamine (8.2g) was heated to reflux in dry ethanol (240 ml) for 16 hours and filtered hot. The filtrate was reduced in volume and the solid so obtained was filtered off. Recrystallisation from ethanol gave the nitropyrimidine oxime (II) (1.17g) as a pale yellow gelatinous solid, m.p. >250° C (decomp.).

v. 2-Amino-4-hydroxy-6-(p-chloro)phenoxymethyl-7,7-dimethyl pteridine (I; R = Ch$_2$OC$_6$H$_4$.Cl, R$^1$ = R$^2$ = CH$_3$)

A solution of 2-amino-4-hydroxy-6-[2-hydroxyimino-1,1-dimethylpropylamino]-5-nitropyrimidine (II) in warm 1M sodium hydroxide was treated with sodium dithionite in portions and the title compound was isolated in analogous manner to the procedure described under Example B(v).

Example E.

2-Amino-4-hydroxy-6-(p-methyl)phenoxymethyl-7,7-dimethyl-7,8-dihydropterdine (I; R = CH$_2$OC$_6$H$_4$.CH$_3$, R$^1$ = R$^2$ = CH$_3$)

i. 1-(p-methyl)phenoxy-3-methylbut-2 ene (VI; R = CH$_2$OC$_6$H$_4$.CH$_3$, R$^1$ = R$^2$ = CH$_3$)

A mixture of p-cresol and sodium hydroxide was stirred with dimethylformamide and water while 1-bromo-3-methylbut-2-ene (VII; R$^1$ = R$^2$ = CH$_3$, Hal = Br) was added dropwise. The 1-(p-methylphenoxy-3-methylbut-2-ene was isolated as described under Example B(i).

ii. 2-Chloro-4-(p-methyl)phenoxy-2-methyl-3-nitrosobutane (V; R = CH$_2$OC$_6$H$_4$.CH$_3$, R$^1$ = R$^2$ = CH$_3$)

Concentrated hydrochloric acid (7.8 ml) was added dropwise over 1.5 hour to a mixture of 1-(p-methyl)-phenoxy-3-methylbut-2-ene (VI; R = CH$_2$OC$_6$H$_4$.CH$_3$, R$^1$ = R$^2$ = CH$_3$) (12.85 g) and amyl nitrite (11.7 ml) in glacial acetic acid (15.6 ml) at −5° to 0° (ice-salt bath). After a further 1 hour at −5° to 0°, the mixture was filtered. The yellow solid so obtained was washed with acetone and recrystallised from acetone to give the nitrosochloride (V) (7.5 g, yield 42%) as white crystals, m.p. 144–5° (decomp.).

iii. 3-Amino-1-(p-methyl)phenoxy-3-methylbutan-2-one oxime hydrochloride (IV; R = CH$_2$OC$_6$H$_4$.CH$_3$, R$^1$ = R$^2$ = CH$_3$)

A suspension of 2-chloro-4-(p-methyl)phenoxy-2-methyl-3-nitrosobutane (V) in dry methanol (120 ml) was heated to reflux and ammonia gas was passed through until all the solid dissolved (2 hours). Filtration and evaporation of solvent gave a brown solid, which was largely freed of impurities by washing with benzene. Recrystallisation fom isopropanol (a small inorganic residue remained) gave the ketoxime hydrochloride (IV) (5.27 g, yield 66%) as colourless crystals, m.p. 217°–8° (decomp.).

iv. 2-Amino-4-hydroxy-6-(2-hydroxyimino-3-(p-methyl)phenoxy-1,1-dimethylpropylamino)-5-nitropyrimidine (II; R = CH$_2$OC$_6$H$_4$.CH$_3$, R$^1$ = R$^2$ = CH$_3$)

A mixture of 3-amino-1-(p-methyl)phenoxy-3-methylbutan-2-one oxime hydrochloride (IV), 2-amino-4-chloro-6-hydroxy-5-nitropyrimidine (III) (Hal = Cl) (1.91 g) and dry triethylamine (4.08 g) was heated to reflux in dry ethanol (120 ml) for 16 hours. The resulting suspension was cooled and filtered. The solid so obtained was partially dissolved in ethanol (500 ml) at reflux. On cooling, the filtered solution deposited the nitropyrimidine oxime (II) as a white gelatinous solid (0.87 g) m.p. >300° (decomp.).

V. 2-Amino-4-hydroxy-6-(p-methyl)phenoxymethyl-7,7-dimethyl-7,8-dihydropteridine

I; R = CH$_2$OC$_6$H$_4$.CH$_3$, R$^1$ = R$^2$ = CH$_3$)

A solution of 2-amino-4-hydroxy-6-[2-hydroxyimino-3-(p-methyl)phenoxy-1,1-dimethylpropylamino]-5- mitropyrimidine (II) (1.2 g) in warm 1 M sodium hydroxide (50 ml) was treated during 10 minutes with sodium dithionite (5 g) until the initial red colour was replaced by a white solid. After hours on a steam bath the suspension was cooled and filtered and the dihydropteridine (1) was precipitated out. It was purified by dissolving it in dimethylsulphoxide, filtering the resulting solution and diluting with water to precipitate the product as a white powder, m.p. >250° (decomp.).

EXAMPLE F

2-Amino-4-hydroxy-6-(p-methoxy)phenoxymethyl-7,7-diethyl-7,8-dihydropteridine (I; $R = CH_2OC_6H_4.OCH_3$, $R^1 = R^2 = C_2H_5$)

i. 1-(p-methoxy)phenoxy-3-ethylpent-2-ene (VI; $R = CH_2OC_6H_4.OCH_3$, $R^1 = R^2 = C_2H_5$)

A solution of p-methoxyphenol (24.5 g) and sodium hydroxide pellets (9 g) in dimethylformamide (200 ml) and water (20 ml) at 60° was treated with 1-bromo-3-ethyl-2-pentent (VII), ($R^1 = R^2 = C_2H_5$) (35 g), added dropwise with stirring over 1-1½hours. The reaction mixture was stirred for a further 4 hours at 60°-65° and then poured into ice-water (750 ml). The mixture was extracted with ether (3×300 ml) and the extract was washed with 10% sodium hydroxide solution (200 ml), water (3×200 ml) and brine (50 ml). It was dried over sodium sulphate. Evaporation of the ether gave a reddish-brown oil which on distillation gave the product (26 g), b.p. 90°-95°/0.2 torr.

ii. 3-Chloro-1-(p-methoxy)phenoxy-3-ethyl-2-nitrosopentane

V; $R = CH_2OC_6H_4.OCH_3$, $R^1 = R^2 = C_2H_5$ 1-(p-methoxy)phenoxy-3-ethyl-pent-2-ene (26 g) (VI) in glacial acetic acid (25 ml) and amyl nitrite (17.7 ml) at 0° was treated with concentrated hydrochloric acid (11.8 ml) added dropwise with stirring over 1 hour. The reaction mixture was stirred for a further 1 hour and the yellow precipitate which had formed was filtered and dried on a porous plate (12.2 g). A portion (1 g) was recrystallised from acetone to give a pale yellow crystalline solid, m.p. 122°-3°.

iii. 3-Amino-1-(p-methoxy)phenoxy-3-ethylpenten-2-one oxime hydrochloride (IV; $R = CH_2OC_6H_4.OCH_3$, $R^1 = R^2 = C_2H_5$)

3-Chloro-1-(p-methoxy)phenoxy-3-ethyl-2-nitrosopentane (V) (11.2 g) was suspended in methanolic-ammonia solution (250 ml) and refluxed whilst ammonia was bubbled through the solution. After 6 hours the methanol-ammonia was removed in vacuo to give a brown gum. Anhydrous benzene (50 ml) was added to dissolve the gum and the addition of petroleum ether 40°-60° (100 ml) precipitated an off-white crystalline solid. This was dissolved in boiling sec-butanol (200 ml), filtered and the filtrate concentrated to a small volume (~50 ml) to yield a crystalline solid (4.3 g), m.p. 190° (dec.).

Concentration of the mother liquors gave a second crop of product (1.7 g).

iv. 2-Amino-4-hydroxy-6-(2-hydroxyimino-3-(p-methoxy)phenoxy-1,1-diethylpropylamino)5-nitropyrimidine (II; $R = CH_2OC_6H_3.OCH_3$, $R^1 = R^2 = C_2H_5$)

A mixture of 3-amino-1-(p-methoxy)phenoxy-3-ethyl-penten-2-one oxime hydrochloride (IV) (4.8 g), 2-amino-4-chloro-6-hydroxy-5-nitropyrimidine (III) (Hal =Cl) (3 g) and triethylamine (5 g) is absolute ethanol (200 ml) was refluxed for 18 hours. The reaction mixture was cooled and the insoluble residue filtered. The filtrate was evaporated to dryness in vacuo to give a pale yellow gum. This was taken up in hot acetone (100 ml) and the residue filtered. The filtrate was concentrated in vacuo to 30 ml and treated with water (150 ml) to precipitate a gum which soldified on refrigeration. This was filtered and dried in vacuo (3.6 g). A portion (0.6 g) was recrystallised from aqueous acetone (in the presence of charcoal) to give an off-white crystalline solid, m.p. >250°. The bulk was taken up in acetone (50 ml), filtered to remove insoluble residue (1 g) and the product was precipitated by the addition of water (50 ml) to give pure product (1.6 g).

v. 2-amino-4-hydroxy-6-(p-methoxy)phenoxymethyl-7,7-diethyl-7,8-dihydropteridine (I; $R = CH_2OC_6H_4.OCH_3$ $R^1 = R_2 = C_2H_5$)

2-Amino-4-hydroxy-6-[2-hydroxyimino-3-(p-methoxy)phenoxy-1,1-diethylpropylamino]-5-nitropyrimidine (II) (0.8 g) in 2N sodium hydroxide (100 ml) was treated with sodium dithionite whilst heating on steambath. The solution turned a reddish-brown and then to pale yellow-green. The reaction mixture was left on a steambath for 45 minutes, then cooled and taken to pH8 with glacial acetic acid to precipitate a colourless flocculent solid. This was filtered to give a tacky colourless solid (0.3 g). Recrystallisation from aqueous alcohol gave an off-white solid (0.08 g).

EXAMPLE G

2-Amino-4-hydroxy-6-(p-chloro)phenoxymethyl-7,7-diethyl-7,8-dihydropteridine (I; $R = CH_2OC_6H_4.Cl$, $R^1 = R^2 = C_2H_5$)

i. 1-(p-chloro)phenoxy-3-ethylpent-2-ene (VI; $R = CH_2OC_6H_4.Cl$, $R^1 = R^2 = C_2H_5$)

A solution of p-chloro-phenol (26.5 g) and sodium hydroxide pellets (9 g) in dimethylformamide (180 ml) and water (25 ml) at 60° was treated with 1-bromo-3-ethyl-2-pentene (VII), ($R^1 =R^2 = C_2H_5$) (36.5 g), added dropwise with stirring over 1-1½hours. The reaction mixture was stirred for a further 4 hours at 60°-65° and then poured into ice-water (750 ml). The mixture was extracted with ether (3 × 300 ml) and the extract was washed with 10% sodium hydroxide solution (200 ml), water (3 × 200 ml) and brine (50 ml).

It was dried over sodium sulphate. The ether was removed in vacuo to give a pale brown oil (36 g) which on distillation gave the product (32.5 g), b.p. 112°-15°/0.6 torr.

ii. 3-Chloro-1-(p-chloro)phenoxy-3-ethyl-2-nitrosopentane (V; R ' $CH_2OC_6H_4.Cl$, $R^1 = R^2 = C_2H_5$)

1-(p-chloro)phenoxy-3-ethylpent-2-ene (VI) (32.5 g) in glacial acetic acid (29 ml) and amyl nitrite (21.6 ml) at 0° was treated with concentrated hydrochloric acid (14.5 ml) added dropwise with stirring over 1 hour. The reaction mixture was stirred at 0° for a further 1 hour and the yellow precipitate which had formed was filtered and dried on a porous plate (19.5 g). It was recrystallised from acetone to give an off-white crystalline solid, (15 g), m.p. 129° (dec.)

iii. 3-Amino-1-(p-chloro)phenoxy-3-ethyl-penten-2-one oxime hydrochloride (IV; $R = CH_2OC_6H_4.Cl$, $R^1 = R^2 = C_2H_5$)

3-Chloro-1-(p-chloro)phenoxy-3-ethyl-2-nitrosopentane (V) (15 g) was suspended in methanolic ammonia solution (300 ml) and refluxed whie ammonia was bubbled through the solution. After 7 hours all the starting mterial had dissolved and the solution was cooled and the methanol-ammonia evaporated in vacuo to give a colourless tacky solid. This was dissolved up in sec-butanol (250 ml) with heating on a steambath, filtered to remove a small amount of insoluble residue and the filtrate concentrated until solid began to be deposited. It was refrigerated overnight to give a crop of colourless crystals (9.2 g). Evaporation of the mother liquors gave a second crop of product (1.5 g). m.p. >200°.

iv. 2-Amino-4-hydroxy-6-(2-hydroxyimino-3-(p-chloro)phenoxy-1,1-diethylpropylamino)-5-nitropyrimidine (II; R = $CH_2OC_6H_4.Cl$, $R^1 = R^2 = C_2H_5$)

A mixture of 3-amino-1-(p-chloro)phenoxy-3-ethyl-penten-2-one oxime hydrochloride (IV) (5 g), 2-amino-4-chloro-6-hydroxy-5-nitropyrimidine (III) (Hal=Cl) (3 g) and triethylamine (5 g) in absolute ethanol (200 ml) was refluxed together for 18 hours. The reaction mixture was cooled and filtered to remove the solid residue (1 g). The filtrate was evaporated in vacuo to dryness to give a pale yellow oil which was then treated with water (150 ml) to precipitate a yellow-brown oil which solidified to give a tacky solid. This was dissolved in hot acetone (80 ml) and the residue filtered. Evaporation of the filtrate gave a gum which rapidly solidified (2.5 g). A portion (0.5 g) was recrystallised from aqueous acetone to give pale yellow needles, m.p. 217° (dec.). The remainder was recrystallised to give pure product (as judged by t.l.c.) (1.4 g).

v. 2-Amino-4-hydroxy-6-(p-chloro)phenoxymethyl-7,7-diethyl-7,8-dihydropteridine (I; R = $CH_2OC_6H_4.C$;. $R^1 = R^2 = C_2H_5$)

2-Amino-4-hydroxy-5-(2-hydroxyimino-3-(p-chloro)-phenoxy-1, 1-diethylpropylamino)-5-nitropyrimidine (0.5 g) in 2N sodium hydroxide (80 ml) was treated with sodium dithionite with heating on the steambath. The solution turned a reddish-brown and then to a pale yellow. The reaction mixture was left for 45 minutes on a steambath and then cooled and taken to pH8 with glacial acetic acid, whereupon the dihydropteridine separated as an off-white solid (0.05 g).

EXAMPLE H

2-Amino-4-hydroxy-6-(p-methyl)phenoxymethyl-7,7-diethyl-7,8-dihydropteridine (I; R = $CH_2OC_6H_4.CH_3$, $R^1 = R^2 = C_2H_5$ i. 1-(p-methyl)phenoxy-3-ethylpent-2-ene (VI; R = $CH_2OC_6H_4.CH_3$, $R^1 = R^2 = C_2H_5$)

A solution of p-cresol (20.8 g) and sodium hydroxide pellets (7.7 g) in dimethylformamide (150 ml) and water (20 ml) at 60°-70° was treated with 1-bromo-3-ethyl-2-pentene (VII) ($R^1 = R^2 = C_2H_5$), (34 g), added dropwise with stirring over 1-1½ hours. The mixture was stirred for a further 4 hours at 60°-65° and then poured into ice-water (750 ml). The mixture was extracted with ether (3 × 300 ml) and the extract was washed with 10% sodium hydroxide (200 ml), water (3 × 200 ml) and brine (50 ml). It was dried with sodium sulphate. Evaporation of the ether solution gave a pale yellow oil (26.6 g) which on distillation gave the product (18 g), b.p. 99°-102°/0.35 torr.

ii. 3-Chloro-1-(p-methyl)phenoxy-3-ethyl-2-nitrosopentane (V; R = $CH_2OH_6H_4.CH_3$, $R^1 = R^2 = C_2H_5$)

1-(p-methyl)phenoxy-3-ethylpent-2-ene (VI) (18 g) in glacial acetic acid (17.6 ml) and amyl nitrite (13.2 ml) at 0° was treated with concentrated hydrochloric acid (8.8 ml) added dropwise over 1 hour. The reaction mixture was stirred at 0° for a further 1 hour and the pale yellow solid which precipitated was filtered and dried on a porous plate (14.5 g). A portion (1 g) was recrystallised from acetone to give a pale yellow crystalline solid, m.p. 129° (dec.).

iii. 3-Amino-1-(p-methyl)phenoxy-3-ethylpenten-2-one oxime hydrochloride (IV; R = $CH_2OC_6H_4.CH_3$, $R^1 = R^2 = C_2H_5$)

3-Chloro-1-(p-methyl)phenoxy-3-ethyl-2-nitrosopentane (13.8 g) was suspended in methanolic-ammonia solution (250 ml) and refluxed whilst ammonia was bubbled through the solution. After 6 hours the methanol-ammonia was removed in vacuo and the residue was treated with acetone (50 ml) to precipitate the crude ketoxime hydrochloride (7 g). This was treated with benzene (50 ml) and the residue was recrystallized from isopropanol to give a colourless crystalline solid (4.8 g).

iv. 2-Amino-4-hydroxy-6-(2-hydroxyimino-3-(p-methyl)phenoxy-1,1-diethylpropylamino)-5-nitropyrimidine (II; R = $CH_2OC_6H_4.CH_3$, $R^1 = R^2 = C_2H_5$)

3-Amino-1-(p-methyl)phenoxy-3-ethyl-penten-2-one oxime hydrochloride (IV), 2-amino-4-chloro-6-hydroxy-5-nitropyrimidine (III) (Hal=Cl) and triethylamine in absolute ethanol were refluxed together for 18 hours. The reaction mixture was cooled and the insoluble residue removed by filtration. The filtrate was evaporated in vacuo to dryness and the title compound was isolated analogously to the procedure described under Example F (iv).

2-Amino-4-hydroxy-6-(p-methyl)phenoxymethyl-7,7-diethyl-b 7,8-dihydropteridine (I; R = $CH_2OC_6H_4,CH_3$, $R^1 = R^2 = C_2H_5$)

2-Amino-4-hydroxy-6-(2-hydroxyimino-3-(p-methyl)-phenoxy-1, 1-diethyl-propylamino)-5-nitropyrimidine (II) in 2N sodium hydroxide was treated with sodium dithionite whilst heating on a steambath. The title compound was isolated analogously to the procedure described under Example F (v).

EXAMPLE I

Starting Material for Examples A - E i. 3-Methyl-2-buten-1-ol (VIII); $R^1=R^2=CH_3$)

A solution of 3,3-dimethylacrylic acid (IX; $R^1=R^2=CH_3$, Y=H) (20 g) in sodium-dried ether (200 ml) was treated dropwise with 64 g of a 70% solution of sodium dihydro-bis(2-methoxyethoxy) aluminate in benzene, the temperature being maintained at 0° until the addition was complete (about 1h). The reaction mixture was stirred for 5h at room temperature, and water was then added slowly. The sodium aluminate which precipitated was filtered off, and the filtrate was extracted with ether (4 × 100 ml). The combined extracts were dried, the solvent was removed, and the residual oil was distilled to give 3-methyl-2-buten-1-ol (VIII) as a colourless liquid, b.p. 54°-55°/25mm Hg.

ii. 1-Bromo-3-methylbut-2-ene (VII, $R^1=R^2=CH_3$, Hal=Br)

3-methyl-2-buten-1-ol (VIII) in dry ether was reacted with phosphorus tribromide following the procedure described below in Example J (ii) to produce 1-bromo-3-methylbut-2-ene (VII), which could be used directly for the preparation of the corresponding compounds of formula (VI).

EXAMPLE J

Starting Material for Examples F - H i. 3-Ethyl-1-penten-3-ol (X; $R^1=R^2=C_2H_5$)

To a solution of vinylmagnesium bromide prepared from 29.2 g magnesium was added a solution of penten-3-one (XI; $R^1=R^2=C_2H_5$) (76 g) in tetrahydrofuran (80 ml) keeping the temperature below 50°. After the addition was complete the reaction mixture was left for 15 h at room temperature, then cooled to 0° and diluted with water (500 ml), added cautiously with vigorous stirring keeping the temperature below 40°. The organic phase was separated and the aqueous phase back-extracted with ether. The extracts were combined and dried wtih magnesium sulphate. The solvent was removed in vacuo and the residue was distilled to give 3-ethyl-1-penten-3-ol (60 g) b.p. 131°-2°.

ii. 1-Bromo-3-ethyl-2-pentene (VII; $R^1=R^2=C_2H_5$, Hal=Br)

3-Ethyl-1-penten-3-ol (X) (25 g) in dry ether (200 ml) was stirred at -10° to -2° under nitrogen. Phosphorus tribromide (35 g) was added dropwise over about 30 minutes and the mixture for a further 3 hours at -10° to 0°, before pouring into icewater (200 ml). The ethereal layer was separated and the aqueous layer back-extracted with ether (150 ml). The combined extracts were then washed with water, saturated sodium bicarbonate and saturated sodium chloride solutions and then dried with magnesium sulphate. The ether was removed in vacuo to give a colourless oil (34 g) which was not distilled but used directly for the preparation of the compounds of formula (VI).

The same product could be obtained using 3-ethyl-2-penten-1-ol (VIII; $R^1=R^2=C_2H_5$) as the starting material for this stage.

EXAMPLE K

Potential pteridine antagonists of formula (1) may be tested by investigating the inhibitory effect they impose on the enzymes responsible for the biosynthesis of dihydropteroic acid (DPtA), namely hydroxymethyldihydropteridine pyrophosphokinase (HMPPS), and dihydropteroate synthetase, hereinafter referred to as 'synthetase'. In the following reaction equations the compounds are referred to by their abbreviated forms defined on page 5 of the specification.

1. HMPPS

2. Synthetase

a. An assay for HMPPS was developed in which the transfer of the terminal phosphate of ATP-$\gamma$-$P^{32}$ to Pt could be monitored and correlated with the amount of inhibition of HMPPS by the compound under test.

The compounds of formula (1) which was under test was incorporated into various formulations comprising metabolites and enzymes contained in test tubes, as indicated in TABLE 1.

The components of the mixture were as follows:

I-2-amino-4-hydroxy-6-hydroxymethyl-7,8-dihydropteridine (HMPt) in a concentration of 800 $\mu$M i.e. micromolar; II-a source of HMPPS, obtained from an extract of E. coli and separated from 'synthetase' on Sephadex C-100, (Registered Trade Mark) according to the method of Richey and Brown in J.Biol. Chem.244, 1582-1592 (1969)

III —3mM ATP -$\gamma$-$P^{32}$.

IV —0.10 M ATP neutralised (unlabelled).

V — 0.02M $MgCl_2.6H_2O$.

VI — 0.1 M $MgCl_2.6H_2O$.

VII — Source of HMPPS and 'synthetase'

VIII — the test compound in a concentration of $0.93 \times 10^{-3}$ M

IX — 0.4mM pAB-$C^{14}$

As shown in TABLE 1, tubes 1 to 9 all contain a source of HMPPS, labelled ATP and 0.02 M $MgCl_2.6H_2O$, tubes 2 to 9 containing in addition HMPt and tubes 4 to 9 further containing the test compound. Control tubes 10 to 12 include a source of both HMPPS and synthetase, unlabelled ATP, 0.1M $MgCl_2.6H_2O$ and labelled pAB.

Tubes 1 to 9 containing the amounts of components shown in the Table, were filled up to 200$\mu$l with distilled water, incubated for 60 minutes at 37° C and then chilled on ice. Dextrose (20$\mu$l containing 72.1 mg/ml) and hexokinase (5$\mu$l containing 2000 units/ml) were added to the solution, which was then allowed to stand at room temperature for 15 minutes. 'Darco-G-60' (Registered Trade Mark) (10 mg) was added to each tube and the contents mixed periodically for 10 minutes. The charcoal was removed through a 'Millipore AP 250 2200' (Registered Trade Mark) filter and the filter was washed with three 10 ml portions of cold water. The charcoal and the filter were then radioactively counted.

The radioactive count from the contents of tubes 2 and 3 was taken as the maximum count, since these tubes contained no test compound and thus gave 0% enzyme inhibition. The percentage inhibition produced by the contents of the remaining tubes could then be calculated by relating their radioactive count to the maximum, as determined above.

The contents of tubes 10 to 12 were chromatographically analysed as described under part (b), and used as controls, tubes 10 and 11 containing no test compound (and hence giving 0% inhibition) being accorded the value of 100%. The percentage inhibition exhibited by the contents of the tubes in part (b) of the experiment could then be calculated in relation to this, by comparing the respectdive chromatograms. (b) The activity of the test compound of formula (I) against 'synthetase' was determined as follows, by monitoring the formation of dihydropteroate $C^{14}$.

A pool of Pt was prepared from ATP neutralised (50$\mu$l, 0.1M), $MgCl_2.6H_2O$(50$\mu$l,0.1M), dithiothreitol (100$\mu$l,0.1M), tris buffer (100$\mu$l,0.4M,pH 8.3), HMPt (25$\mu$l,876$\mu$M) and 170$\mu$l. of a solution containing HMPPS. The mixture was incubated for 60 minutes at 37° C, chilled briefly on ice and then dextrose (100$\mu$l containing 72.1mg/ml) and hexokinase (20$\mu$l containing 2000 units/ml) were added at room temperature to the solution, which was allowed to stand at this temperature for 15 minutes.

A solution of $MgCl_2.6H_2O$ (10$\mu$l,0.1M), pAB-$C^{14}$ (10$\mu$l,0.4mM), dithiothreitol (20$\mu$l,0.1M) and tris buffer (20$\mu$l,0.4M,pN8.3) was made in each of five test tubes and then 80$\mu$l of the contents of the pool added to each, together with synthetase and/or test compound of formula (I) as indicated in Table 2. The solution was then made up to 200$\mu$l with distilled water.

Two control test tubes were prepared, each containing ATP (10$\mu$l,0.1M), $MgCl_2.6H_2O$(10$\mu$l,0.1M), dithiothreitol (20$\mu$l,0.1M) tris buffer (20$\mu$l,0.4M,pH 8.3), pAB-C$^{14}$(10μl, 0.4mM), and 20μl of a solution containing HMPPS and 'synthetase' of known activity. The test compound was added to the second of these two tubes up to a final concentration of 10$^{-5}$M, and both tubes were made up with distilled water to 200μl.

All seven tubes were then incubated for 30 minutes at 37° C, chilled on ice and then these, together with control tubes 10 to 12 from part (a), were chromatographically analysed as follows.

100μl of the contents of each of the tubes was spotted onto Whatman no. 3MM chromatography paper (2×20 cm) at the origin, the run descending in a Sorenson buffer of potassium and sodium phosphates (0.1M, pH 7.00 for 10 to 15 cm. From the relative positions of the spots obtained from the contents of the different tubes, the various percentage inhibitions of synthetase could be evaluated by reference to control tubes 10 and 11, which gave 0% inhibition.

Those compounds which, as result of these tests, were found to give 50% inhibition at a concentration of 100μM or less, are those which exert a useful potentiating effect, and subject to their toxicity being favourable, may be included in the compositions described in this specification.

2-Amino-4-hydroxy-6-phenoxymethyl-7,8-dimethyl-7,8-dihydropteridine was found to give 50% inhibition at a concentration of 17 μM.

EXAMPLE L

Tablet Formulation
Compound of formula
(I)(R=CH$_2$Ph;R$^1$=R$^2$=Me) (pure): 100 mg
Trimethoprim (pure): 25 mg
Sulfaguanidine (B.P.C.): 100 mg
+ cornstarch, lactose, gelatin, talcum and magnesium stearate Preparation - the above constituents were mixed together using known methods of pharmacy to form a granulation which was then compressed into tablets.

EXAMPLE M

Table Formulation
"Pyremathimine" (Pyrimethamine) B.P.: 15 mg
Compound of formula
(I)(R=CH$_2$Ph;R$^1$=R$^2$=Me) (pure): 150 mg
which was then prepared to form a tablet as in Example L.

EXAMPLE N

Tablet Formulation
Sulfanilamide B.P.C.: 150 mg
Compound of formula
(I)(R=CH$_2$Ph;R$^1$=R$^2$=Me) (pure): 175 mg
which was then prepared to form a tablet as in Example L.

EXAMPLE O.

Capsule Formulation
Trimethoprim (pure): 20 mg
Compound of formula
(I)(R=CH$_2$Ph;R$^1$=R$^2$=Me) (pure): 100 mg Preparation-The compounds in granular form were blended together with lactose, cornstarch and magnesium stearate. The powder was filled into a two-piece, hard shell gelatin capsule using a capsulating machine.

EXAMPLE P

Irrigant Solution
Compound of formula (I)
(R=CH$_2$Ph;R$^1$=R$^2$=Me) (pure): 1mg/ml
Trimethoprim (pure): 0.2mg/ml
Solvent; water

EXAMPLE Q

Irrigant Solution
Compound of formula (I)
(R=CH$_2$Ph;R$^1$=R$^2$=Me) (pure): 2mg/ml
α-amino-p-toluenesulphonamide (pure): 2mg/ml

EXAMPLE R

| Solution | |
|---|---|
| Compound of formula (I) (R=CH$_2$Ph;R$^1$=R$^2$=Me) (pure) | 1.5 mg/ml |
| Diaveridine B. Vet C | 0.5 mg/ml |
| Kelfizina | 1.0 mg/ml |
| Solvent | water |

EXAMPLE S

| Tablet Formulation | |
|---|---|
| Compound of formula (I) (R=CH$_2$Ph;R$^1$=R$^2$=Me) (pure) | 500 mg |
| Microcrystalline cellulose | 100 mg |
| Starch | 40 mg |
| Magnesium stearate | 10 mg |
| Methylhydroxyethylcellulose | 3 mg |
| | 653 mg |

The pteridine (I), microcrystalline cellulose and starch were granulated with a solution of the methylhydroxyethylcellulose in 50% aqueous ethyl alcohol. The magnesium stearate was added to the dried granules, and the whole then compressed.

TABLE 1

| Tube No. | I | II | III | IV | V | VI | VII | VIII Final Concn. |
|---|---|---|---|---|---|---|---|---|
| 1 | — | 100μl | 15μl | — | 10μl | — | — | — |
| 2 | 5μl | " | " | — | " | — | — | — |
| 3 | " | " | " | — | " | — | — | — |
| 4 | " | " | " | — | " | — | — | 2.5×10$^{-6}$M |
| 5 | " | " | " | — | " | — | — | " |
| 6 | " | " | " | — | " | — | — | 1.0×10$^{-5}$M |
| 7 | " | " | " | — | " | — | — | " |
| 8 | " | " | " | — | " | — | — | 9.3×10$^{-5}$M |
| 9 | " | " | " | — | " | — | — | " |
| Controls | | | | | | | | |
| 10 | — | — | — | 10μl | — | 10μl | 20μl | |
| 11 | 5μl | — | — | " | — | " | " | |
| 12 | " | — | — | " | — | " | " | 1.0×10$^{-5}$M |

TABLE 2

| Tube No. | Excess Synthetase | Test compound Final Concentration |
| --- | --- | --- |
| 1 | − | − |
| 2 | + | − |
| 3 | + | $8.7 \times 10^{-5}$M |
| 4 | + | $1.0 \times 10^{-5}$M |
| 5 | + | $2.5 \times 10^{-6}$M |
| Controls | | |
| 6 | − | − |
| 7 | − | $1.0 \times 10^{-5}$M |

What we claim is:

1. A compound of formula (I), or a tautomeric form thereof,

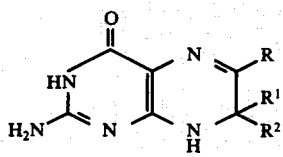

(I)

wherein R is a phenoxyloweralkyl group or phenoxyloweralkyl which is substituted by one or more loweralkoxy, loweralkyl, amino, hydroxyl or halogen and $R^1$ and $R^2$ are the same or different and each is a lower alkyl group or $R^1$ and $R^2$, together with the carbon atom in the pteridine ring structure, form a spriocycloalkyl ring system having 4 to 6 carbon atoms outside the pteridine ring structure.

2. A compound as claimed in claim 1, wherein R is a phenoxyloweralkyl group.

3. A compound as claimed in claim 2, wherein R is a phenoxymethyl group.

4. A compound as claimed in claim 1, wherein R is a phenoxyloweralkyl group substituted with one or more alkoxy, amino, lower alkyl or hydroxy groups or halogen atoms.

5. A compound as claimed in claim 4, wherein the phenoxyloweralkyl group is substituted with a methoxy group.

6. A compound as claimed in claim 4, wherein the phenoxyloweralkyl group is substituted with a methyl group.

7. A compound as claimed in claim 4, wherein the phenoxyloweralkyl group is substituted with a chlorine atom.

8. A compound as claimed in claim 1 wherein the phenoxyloweralkyl group is substituted in the para position.

9. A compound as claimed in claim 1, wherein $R^1$ and $R^2$ are lower alkyl groups.

10. A compound as claimed in claim 9, wherein the alkyl groups are the same and are methyl groups.

11. A compound as claimed in claim 9, wherein the alkyl groups are the same and are ethyl groups.

12. 2-Amino-4-hydroxy-6-phenoxymethyl-7,7-dimethyl-7,8-dihydropteridine or a tautomer thereof.

13. A pharmaceutically acceptable salt of a compound of formula (I), as defined in claim 1; or a tautomeric form thereof.

14. A salt as claimed in claim 13 of a base or a mineral or organic acid.

15. A salt as claimed in claim 14, wherein the mineral acid is hydrochloric acid.

16. The compound of claim 1 wherein $R^1$ and $R^2$, together with the carbon atom in the pteridine ring structure, form a spirocycloalkyl ring system having 4 to 6 carbon atoms outside the pteridine ring structure.

* * * * *